(12) United States Patent
Wu et al.

(10) Patent No.: US 10,548,552 B2
(45) Date of Patent: Feb. 4, 2020

(54) METHOD AND DEVICE FOR GENERATING ANATOMICAL LABELS FOR A PHYSIOLOGICAL TREE STRUCTURE

(71) Applicant: BEIJING CURACLOUD TECHNOLOGY CO., LTD., Beijing (CN)

(72) Inventors: Dan Wu, Bellevue, WA (US); Xin Wang, Seattle, WA (US); Youbing Yin, Kenmore, WA (US); Yuwei Li, Bellevue, WA (US); Kunlin Cao, Kenmore, WA (US); Qi Song, Seattle, WA (US); Bin Ouyang, Shenzhen (CN); Shuyi Liang, Shaoguan (CN)

(73) Assignee: SHENZHEN KEYA MEDICAL TECHNOLOGY CORPORATION, Shenzhen (CN)

(*) Notice: Subject to any disclaimer, the term of this patent is extended or adjusted under 35 U.S.C. 154(b) by 0 days.

(21) Appl. No.: 16/116,889

(22) Filed: Aug. 29, 2018

(65) Prior Publication Data

US 2019/0192096 A1 Jun. 27, 2019

Related U.S. Application Data

(60) Provisional application No. 62/608,872, filed on Dec. 21, 2017.

(51) Int. Cl.
*G06K 9/00* (2006.01)
*A61B 6/00* (2006.01)
(Continued)

(52) U.S. Cl.
CPC ............ *A61B 6/504* (2013.01); *A61B 5/0073* (2013.01); *A61B 5/02007* (2013.01); *G06T 7/10* (2017.01);
(Continued)

(58) Field of Classification Search
None
See application file for complete search history.

(56) References Cited

U.S. PATENT DOCUMENTS

| 9,349,178 B1* | 5/2016 | Itu ......................... G16H 50/50 |
| 2013/0216110 A1* | 8/2013 | Zheng ..................... G06K 9/34 |
| | | 382/128 |
| 2017/0213339 A1* | 7/2017 | Hibbard .................... G06T 7/38 |

OTHER PUBLICATIONS

Feragen ("Geodesic Atlas-Based Labeling of Anatomical Trees: Application and Evaluation on Airways Extracted From CT", IEEE, pp. 1212-1226, Jun. 2015) (Year: 2015).*

(Continued)

*Primary Examiner* — Wei Wen Yang
(74) *Attorney, Agent, or Firm* — Bayes PLLC (57) ABSTRACT

The present disclosure is directed to a method and device for generating anatomical labels for a physiological tree structure. The method may include receiving a 3D model and a 3D skeleton line of the physiological tree structure. The 3D model is restructured based on medical image data of the physiological tree structure acquired by an imaging device. The method further includes selecting at least one level from extracting geometrical features from a pool of selectable levels. The method also includes extracting, by a processor, geometrical features from the 3D model of the physiological tree structure along the 3D skeleton line at the selected at least one level. The method also includes generating, by the processor, anatomical labels for the physiological tree structure using a trained learning network based on the extracted geometrical features.

19 Claims, 10 Drawing Sheets

(51) Int. Cl.
| | |
|---|---|
| *G16H 30/40* | (2018.01) |
| *A61B 5/00* | (2006.01) |
| *G06T 7/10* | (2017.01) |
| *A61B 5/02* | (2006.01) |
| *G06T 19/00* | (2011.01) |
| *G16H 50/50* | (2018.01) |

(52) U.S. Cl.
CPC .............. *G16H 30/40* (2018.01); *G06T 19/00* (2013.01); *G06T 2207/30101* (2013.01); *G16H 50/50* (2018.01)

(56) References Cited

OTHER PUBLICATIONS

Zheng (US 20130216110 A1), and Zhang ("Automatic Anatomical Labeling of Abdominal Arteries for Small Bowel Evaluation on 3D CT Scans", IEEE, pp. 210-213, Apr. 2013). (Year: 2013).*
A. Akinyemi, S. Murphy, I. Poole, and C. Roberts, "Automatic labelling of coronary arteries," in 2009 17th European Signal Processing Conference, 2009, pp. 1562-1566.
M. A. Gülsün, G. Funka-Lea, Y. Zheng, and M. Eckert, "CTA Coronary Labeling through Efficient Geodesics between Trees Using Anatomy Priors," in Medical Image Computing and Computer-Assisted Intervention—MICCAI 2014, 2014, pp. 521-528.
G. Yang et al., "Automatic coronary artery tree labeling in coronary computed tomographic angiography datasets," in 2011 Computing in Cardiology, 2011, pp. 109-112.

* cited by examiner

METHOD AND DEVICE FOR GENERATING ANATOMICAL LABELS FOR A PHYSIOLOGICAL TREE STRUCTURE

CROSS-REFERENCE TO RELATED APPLICATION

This application claims the benefit of priority to U.S. Provisional Application No. 62/608,872, filed on Dec. 21, 2017, the entire contents of which are incorporated herein by reference.

TECHNICAL FIELD

The disclosure generally relates to medical image processing and analysis. More specifically, this disclosure relates to a method and device for generating anatomical labels for a physiological tree structure.

BACKGROUND

Blood vessels, tracheal pathways, and the like are all hierarchical tree structures. Automatically identifying and assigning correct anatomical labels to these structures facilitates the diagnostic process for physicians and radiologists. Extant methods of automatically generating medical reports generally rely on correct identification of anatomical labels (such as coronary artery vessels, bronchial trees, and the like) and correct assignment of labels based on the identification. Diagnoses may depend on the accuracy of the identification and labeling. For example, the anatomical location of a stenosis often suggests the severity of its effect on the normal functionality of the heart. Accordingly, if a stenosis is detected by extant algorithms, it is important to identify where it is located, which may depend on automatically identifying the correct anatomical labels for the corresponding vessel (e.g., a left anterior descending artery).

As one example, anatomically meaningful coronary artery supplies a specific area of the myocardium, but the morphology and topology of these arteries vary widely on an individual basis. Therefore, one challenge of automatic labeling arises from the large individual variability of coronary anatomy, especially with regards to some of the secondary arteries emerging from the main branches. Such complexity also challenges labeling of other vessels in the human body, other than coronary arteries.

Extant methods are also not sufficiently reliable with regards to large individual variability. Generally, extant methods typically rely on a human coronary atlas model based on statistical results of a limited number of human coronary arteries or on hard coded geometrical or topological criteria and/or parameters. Due to the individual variability, such methods are less robust in labeling the vessels.

This disclosure provides a method and device that may quickly, accurately, and automatically generate anatomical labels for a physiological tree structure. The method and device increase the robustness and accuracy of automatically labeling by using learning networks (such as a neural network), which are able to learn essential anatomical characteristics without any human defined criteria and also continuously improve performance with increasing data. Besides, the method and device may select (or vary) the level of the geometrical features to be extracted and fed into the learning network, so as to satisfy the needs on labeling speed, resource consuming, and granular accuracy.

SUMMARY

In one aspect, the present disclosure is directed to a computer-implemented method for generating anatomical labels for a physiological tree structure. The method may include receiving a 3D model and a 3D skeleton line of the physiological tree structure. The 3D model is reconstructed based on medical image data of the physiological tree structure acquired by an imaging device. The method further includes selecting at least one level from extracting geometrical features from a pool of selectable levels. The method also includes extracting, by a processor, geometrical features from the 3D model of the physiological tree structure along the 3D skeleton line at the selected at least one level. The method further includes generating, by the processor, anatomical labels for the physiological tree structure using a trained learning network based on the extracted geometrical features.

In another aspect, the present disclosure is directed to a device for generating anatomical labels for a physiological tree structure. The device may include an interface configured to receive medical image data of the physiological tree structure acquired by an imaging device. The device may also include a processor configured to reconstruct a 3D model and extract a 3D skeleton line of a physiological tree structure based on the received medical image data. The processor may be further configured to select at least one level from extracting geometrical features from a pool of selectable levels, and extract geometrical features from the 3D model of the physiological tree structure along the 3D skeleton line at the selected at least one level. Further, the processor may be configured to generate anatomical labels for the physiological tree structure using a trained learning network based on the extracted geometrical features.

In yet another aspect, the present disclosure is directed to a non-transitory computer readable medium having instructions stored thereon. The instructions, when executed by a processor, perform a method for generating anatomical labels for a physiological tree structure. The method may include receiving a 3D model and a 3D skeleton line of the physiological tree structure. The 3D model is reconstructed based on medical image data of the physiological tree structure acquired by an imaging device. The method further includes selecting at least one level from extracting geometrical features from a pool of selectable levels. The method also includes extracting geometrical features from the 3D model of the physiological tree structure along the 3D skeleton line at the selected at least one level. The method further includes generating anatomical labels for the physiological tree structure using a trained learning network based on the extracted geometrical features.

It is to be understood that the foregoing general description and the following detailed description are exemplary and explanatory only, and are not restrictive of the invention, as claimed.

BRIEF DESCRIPTION OF THE DRAWINGS

In the drawings, which are not necessarily drawn to scale, like numerals may describe similar components in different views Like numerals having letter suffixes or different letter suffixes may represent different instances of similar components. The drawings illustrate generally, by way of example, but not by way of limitation, various embodiments, and together with the description and claims, serve to explain the disclosed embodiments. When appropriate, the same reference numbers are used throughout the drawings to refer to the same or like parts. Such embodiments are demonstrative and not intended to be exhaustive or exclusive embodiments of the present method, system, or non-transitory computer readable medium having instructions thereon for implementing the method.

DETAILED DESCRIPTION

Hereinafter, the technical expression "extract features . . . along the 3D skeleton line" means to extract features for the 3D model of the physiological tree structure at a sequence of parts along the 3D skeleton line. Particularly, several parts may be sampled from the 3D model along the 3D skeleton line, and each part has the corresponding local feature(s) of the 3D model. Then all the local feature(s) may comprise the features extracted along the 3D skeleton line (of a physiological tree structure). And the technical term "medical image data of the physiological tree structure" means medical image data including at least part of the physiological tree structure therein. For example, the medical image data may be a sequence of 2D slides for a vessel tree structure acquired by CT. For another example, the medical image data may be at least two 2D vessel angiography images from different projection angles. For still another example, the medical image data of the physiological tree structure may include multiple subsets of medical image data of different parts of the physiological tree structure, which may be integrated to reconstruct the 3D model of whole physiological tree structure. Further, the technical term "geometrical feature" refers to a feature associated with the geometry factors of the subject (e.g. the physiological tree structure), including but not limited to the coordinate, direction, shape, size, etc. of at least part of the subject.

Figure 1:
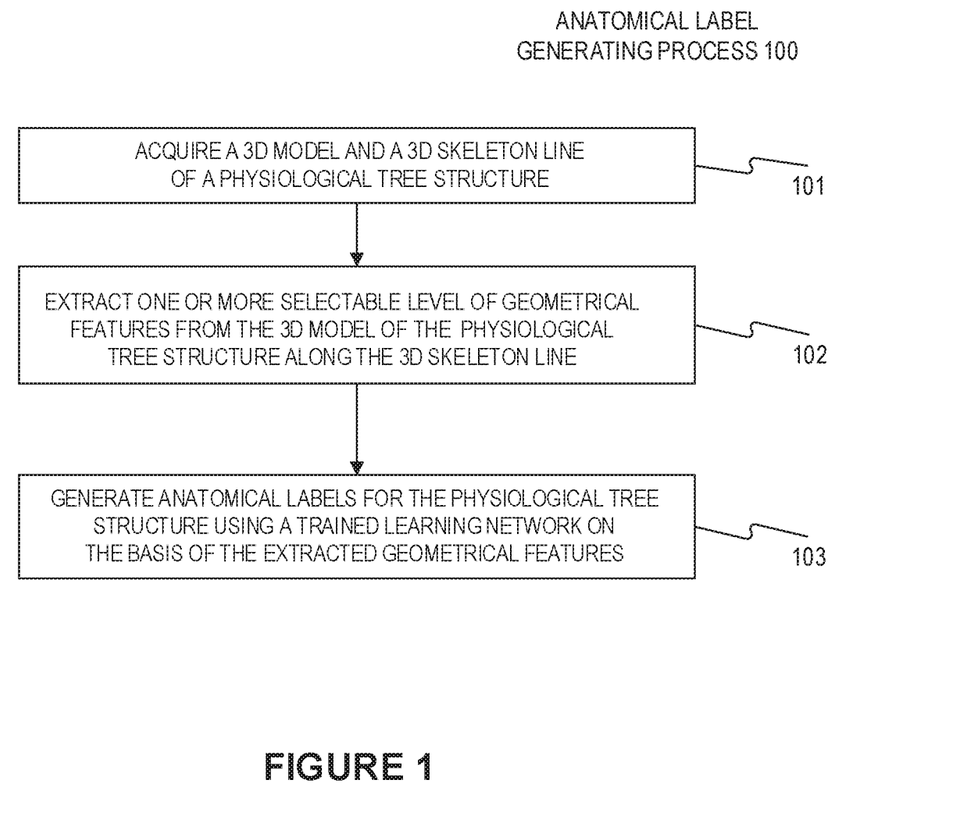
FIG. 1 illustrates a method for generating anatomical labels for a physiological tree structure according to an embodiment of present disclosure.

FIG. 1 illustrates a method for generating anatomical labels for a physiological tree structure according to an embodiment of present disclosure. As shown in FIG. 1, the anatomical label generating process 100 begins with acquiring a 3D model and a 3D skeleton line of a physiological tree structure (step 101). In some embodiments, the 3D model and the 3D skeleton line may be acquired directly from the existing 3D reconstruction applications which may be already installed in the medical image acquisition device, such as but not limited to OpenGL, Syngo® DynaCT Cardiac from Siemens Healthcare, etc., and the computer-implemented method for generating anatomical label may be compatible with and make use of the existing 3D reconstruction applications. In some embodiments, at step 101, the medical image data (e.g., 2D medical images) of the physiological tree structure may be received from imaging acquisition device, and then the 2D medical images may be segmented and processed to reconstruct the 3D model and derive the 3D skeleton line. At step 102, one or more selectable level of geometrical features may be extracted from the 3D model along the 3D skeleton line. Then the anatomical label generating process 100 proceeds to step 103. At step 103, the anatomical labels may be generated for the physiological tree structure using a trained learning network based on the extracted geometrical features.

The 3D skeleton line represents the profile of the physiological tree structure. For example, the 3D skeleton line may be a centerline of a human coronary artery 3D model. For another example, the 3D skeleton line may be a topology extending line of the nervous tissue.

In some embodiments, the level of the extracted geometrical features may be selected from a point to a path. The physiological tree structure is a hierarchical tree structure. In this structure, a point refers to a point on the 3D skeleton line while a path refers to a passage from an inlet of the 3D skeleton line to an outlet of the 3D skeleton line. Median level, which is higher than the point but is lower than the path, may be adopted for the geometrical features to be extracted as well. Taking the coronary artery as an example for the physiological tree structure, centerline of the 3D model of the coronary artery may be computed and extracted as the 3D skeleton line. For example, the geometrical features may be stored in three levels of structural information, e.g., centerline point, centerline cell, and centerline path. The centerline cell may refer to vessel branches between bifurcations, and the centerline path may refer to a path from an inlet to an outlet of the centerline. For example, a Y-shaped centerline has two paths, each of which begins with a different inlet but ends at the same outlet.

In some embodiments, the one or more levels used for the extracted geometrical features in step 102 may be selected and varied based on at least one of the computing speed, computing resource, and granular accuracy. If the user needs to obtain the anatomical label with limited computing resource and less granular accuracy, for example, if the user only needs to know the anatomical label for a vessel path, and/or the user has a high requirement on the computing speed, then higher levels of geometrical features, such as path-wise features, may be used and less physiological tree structure characteristics need to be learned by the learning network. As a contrast, if the user needs to obtain the anatomical label with more granular accuracy, then lower levels of geometrical features, such as point-wise features, may be used and more physiological tree structure characteristics need to be learned by the learning network. In some embodiments, the level of the geometrical features extracted in step 102 is the same or lower than the level of the anatomical labels generated at step 103, so as to ensure the reliability of the generated anatomical labels. That is to say, if a cell-wise accuracy is needed, then point-wise feature and/or cell-wise feature needs to be extracted. Besides, if the computing resource is sufficient and/or the computing speeds for a higher level of anatomical label and a lower level of anatomical label makes unobvious difference to the user, then lower levels of geometrical features (the same or lower than the lower level of anatomical label) may be extracted and the corresponding learning network may be adopted.

In some embodiments, multiple types of geometrical features may be extracted at each level. For a coronary artery, the point-wise features may include at least one of normalized 3D coordinates (e.g. x, y, z coordinates normalized by maximum and/or minimum of x, y, z coordinates respectively within the 3D model), normal direction, 2D spherical coordinates, local average radius (e.g. obtained from local cross-sectional area by assuming circular local cross-section of the coronary artery), normalized downstream volume (e.g. total volume of all downstream branches starting from a point of interest on the 3D model, and normalized by the total volume of the 3D model), length from root, etc. of a point on the 3D centerline. The cell-wise features may include at least one of average length, average volume, starting point, tortuosity, branch angle with parent branch, center points, 2D spherical coordinates, etc. of a cell on the 3D centerline. The path-wise features may include at least one of normalized length (e.g. length normalized by the longest path of the 3D model), total volume, tortuosity, center points, 2D spherical coordinates, average branch angle, etc. of a path on the 3D centerline.

Figure 2:
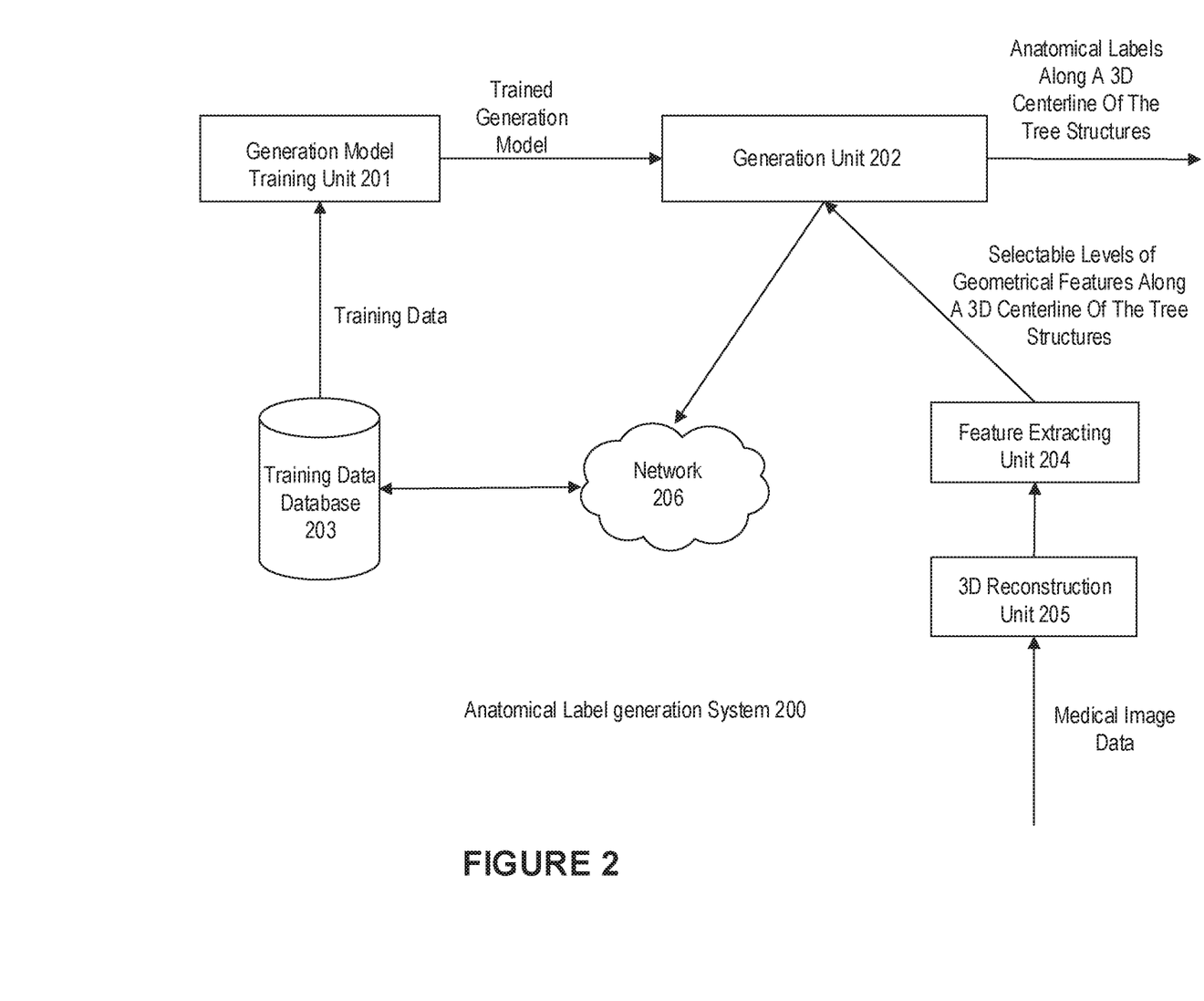
FIG. 2 illustrates an anatomical label generation system according to an embodiment of present disclosure.

FIG. 2 illustrates an anatomical label generation system 200 according to an embodiment of present disclosure, wherein centerline is used as an example of the skeleton line. As shown in FIG. 2, the anatomical label generation system 200 may include: a 3D reconstruction unit 205, which is configured to acquire medical image data of the tree structures, reconstruct a 3D model for the same, and extract a corresponding 3D centerline; a feature extracting unit 204, which is configured to receive the reconstructed 3D model and 3D centerline from the 3D reconstruction unit 205, and extract selectable level(s) of geometrical features along the 3D centerline based on the 3D model; a generation model training unit 201, which is configured to train the anatomical label generation model (which is constructed based on learning network, especially multilayer neural network) based on training data(set), and transmit the trained generation model to a generation unit 202; and the generation unit 202, which is configured to receive the trained generation model from the generation model training unit 201 and selectable level(s) of geometrical features along a 3D centerline of the tree structures from the feature extracting unit 204, and generate the anatomical labels along the 3D centerline of tree structure using the trained generation model based on the extracted geometrical features. In some embodiments, the feature extracting unit 204 may be integrated with the 3D reconstruction unit 205.

In some embodiments, the generating model training unit 201 may adopt off-line training process and/or on-line training process. The off-line training process may be performed prior to and not in real time with the label generating process based on the training data from a training data database 203. The training data for off-line training process may be obtained by multi-level feature (such as point-wise features, cell-wise features, path-wise features, and the like) extracting from the 3D model reconstructed based on the medical image data and manual labeling by the user (such as the physician) on the 3D model (as the ground truth anatomical label). The obtained training data may be collected and stored into the training data database 203 to be accessed and utilized by other users. The on-line training process may be performed in real-time just prior to or in parallel with the label generating process. Particularly, the anatomical labels along the 3D centerline generated by the generation unit 202 (or in combination with manual corrections of the user) together with the corresponding extracted geometrical features may be used as fresh training data to train the generation model in an on-line manner. Besides, such fresh training data may be added into the training data database 203 to update it for later off-line training process.

In some embodiments, the off-line training process may be used to train a reference label generation model for a new tree structure, for which no label generation has been performed. For example, the off-line training process may utilize training data for a coronary artery of Asian women in their thirties with a BMI 22-27 to train a reference label generation model for this specific population. Then, if the user needs to generate the anatomical labels for a patient belonging to this specific population, the trained reference label generation model may be recalled conveniently and used for generating the anatomical labels along the 3D centerline of the coronary artery. In some embodiments, the automatically generated anatomical labels may be presented to the user, so as to receive his/her on-line feedbacks, e.g., confirmations, manual edits, and corrections, etc. The resulted anatomical labels upon the on-line feedback may be used as fresh training data to update the existing weights in the current trained generation model (e.g. the trained reference label generation model) in an on-line manner. Thereby, the anatomical label generation model specific for the user may be improved continuously with additional training data and benefit from on-line feedbacks. The improved trained anatomical label generation model for the specific user may be recalled directly for his/her anatomical label generation later.

Figure 3:
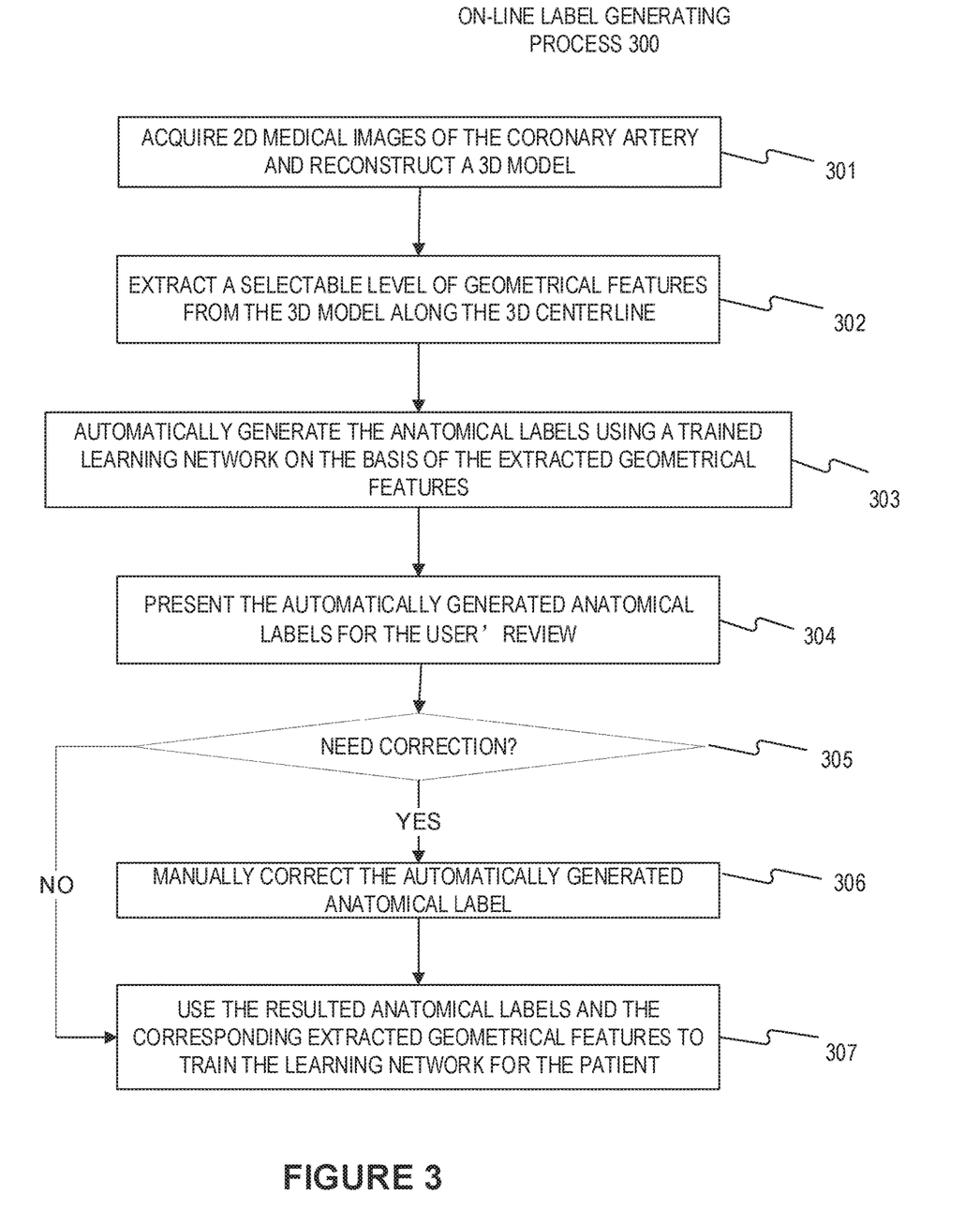
FIG. 3 illustrates an on-line label generating process according to an embodiment of present disclosure.

FIG. 3 illustrates an on-line label generating process 300 for a coronary artery according to an embodiment of present disclosure. The coronary artery is used only as an example of the physiological tree structure; the process may be adapted to other physiological tree structures, such as blood vessels, tracheal pathway, lymphatic vessels, and nervous tissue.

The on-line label generating process begins with step 301: acquiring medical image data (e.g., 2D medical images or volumetric images) of the coronary artery and reconstructing a 3D model thereof. The medical image data may be acquired by an imaging device (also referred to as an image acquisition device). The imaging device may use any imaging modality, including, but not limited to, CT, digital subtraction angiography (DSA), MRI, functional MRI, dynamic contrast enhanced-MRI, diffusion MRI, spiral CT, cone beam computed tomography (CBCT), positron emission tomography (PET), single-photon emission computed tomography (SPECT), X-ray imaging, optical tomography, fluorescence imaging, ultrasound imaging, radiotherapy portal imaging. The 3D model of the coronary artery usually represents its 3D geometry and the positional relationships among the points therein or on the wall of the coronary artery. For example, a sequence of 2D slice images along the coronary artery may be acquired by CT, and each 2D slice image may be segmented to extract the center point and the vessel wall. Then, the 3D model may be reconstructed based on the extracted center point and vessel wall of each 2D slice image of the sequence and the 3D centerline may be established based on the extracted center point of each 2D slice image of the sequence. In this example, the 3D centerline is acquired at step 301. For another example, volumetric imaging such as volumetric CT imaging may be adopted to acquire 3D image data directly, and the 3D centerline thus may be acquired at a subsequent step, such as step 302.

Then, at step 302, a selectable level of geometrical features may be extracted from the 3D model of the coronary artery along the 3D centerline. The details on the selectable level and the geometrical feature have been given as above in combination with FIG. 1, and thus are omitted here. At step 303, anatomical labels for the coronary artery may be automatically generated using a trained learning network (examples of which are illustrated by FIG. 5(a)~FIG. 5(e)) based on the extracted geometrical features. The anatomical label to be generated may be of a selectable level as needed, including but not limited to a path label and a cell label. For a coronary artery, in some embodiments, the cell labels may include left main artery (LM), left anterior descending artery (LAD), left circumflex artery (LCX), diagonal artery (D), septal artery (S), obtuse margin artery (OM), right coronary artery (RCA), posterior descending artery (PDA), left posterior lateral branch (L-PLB) and right posterior lateral branch (R-PLB). In some embodiments, the path labels may include left anterior descending artery path (LAD), left circumflex artery path (LCX), obtuse margin artery path (OM), diagonal artery path (D), septal artery path(S), right coronary artery path (RCA), posterior descending artery path (PDA), left posterior lateral branch path (L-PLB) and right posterior lateral branch path (R-PLB). In some embodiments, the path label and cell label may be converted into one another. For example, the cell labels of the cells included by a path may be regressed to obtain the path label for the path. Particularly, among all the cell labels of the cells within the path, the cell label with the maximum number may be determined as the path label. For another example, the path label may be used as the cell label for each cell therein.

Figure 4:
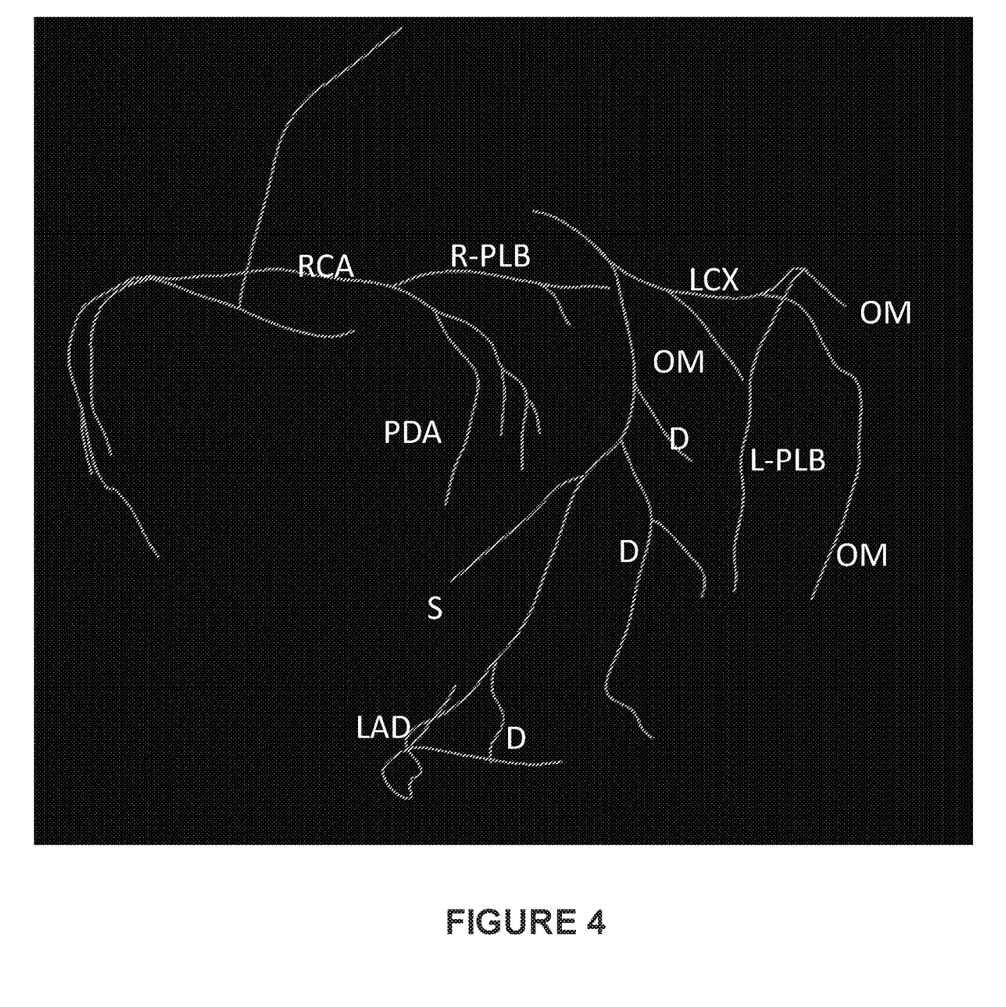
FIG. 4 illustrates a vessel tree structure which is labeled with that generated by the process as shown in FIG. 3.

Optionally, the process 300 may include a step 304, wherein in response to generating anatomical labels, the generated anatomical labels may be presented adjacent to the corresponding part of the coronary artery, as shown in FIG. 4, for the user's review. In some embodiments, the user may confirm whether the automatically generated labels need correction (step 305). If so, the user may edit, modify, and move the generated anatomical labels by means of a user interface (step 306). Then the process 300 turns to step 307, the resulted anatomical labels and the corresponding extracted geometrical features may be used as fresh training data to train the current learning network for the patient in an on-line manner. Thereby, the performance of the learning network for a specific patient may be improved as more fresh training data for the specific patient are obtained. By means of integrating the automatic generation with artificial correction, the resulted anatomical labels may be consistent with the ground truth labels, thus accurate training data may be obtained meanwhile reducing work load compared to fully manual labeling and consuming less computing resource compared to fully automatic labeling.

If it is the first time to automatically generate the anatomical labels for the coronary artery of the patient, then a trained reference learning network may be retrieved and used at step 303. The weights of the trained learning network may be stored and updated for the patient. In this manner, if the process 300 has been performed for the patient before, then the learning network trained by the step 307 of the latest process 300 for the patient may be used at step 303 of current process 300.

Figure 5A:
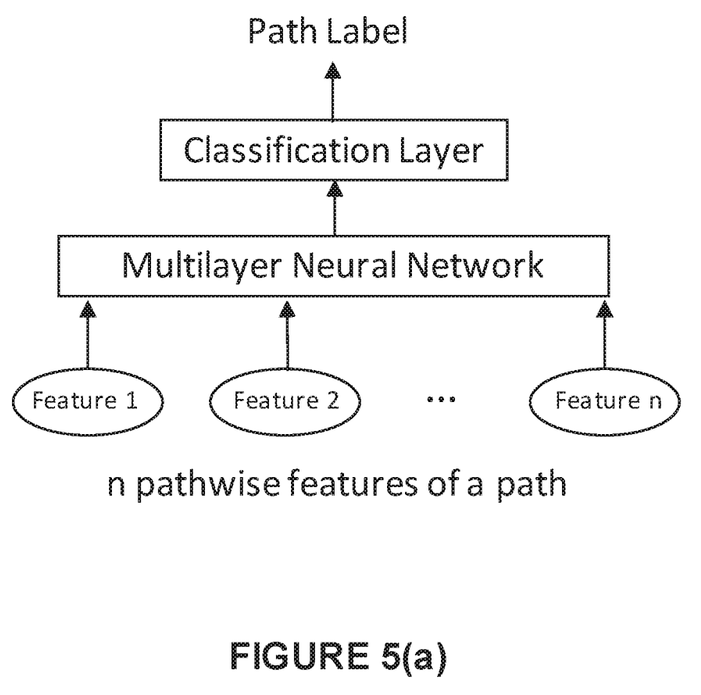
FIG. 5(a) illustrates an example of the learning network used in the method according to an embodiment of present disclosure.

FIG. 5(a) illustrates an example of the learning network used in the method according to an embodiment of present disclosure, e.g. the on-line label generating process 300. In some embodiments, multiple types of geometrical features may be adopted for a single level. As shown in FIG. 5(a), the path is set as the feature level, and n geometrical features (path-wise features) may be adopted for each path. In this learning network, the n path-wise geometrical features of each path may be fed into a multi-layer neural network, which may include or cooperate with a classification layer, so as to determine the path label. The classification layer may be implemented by various manners. For example, it may be constructed by RNN (regression neural network), fully connected layer, etc.

Figure 5B:
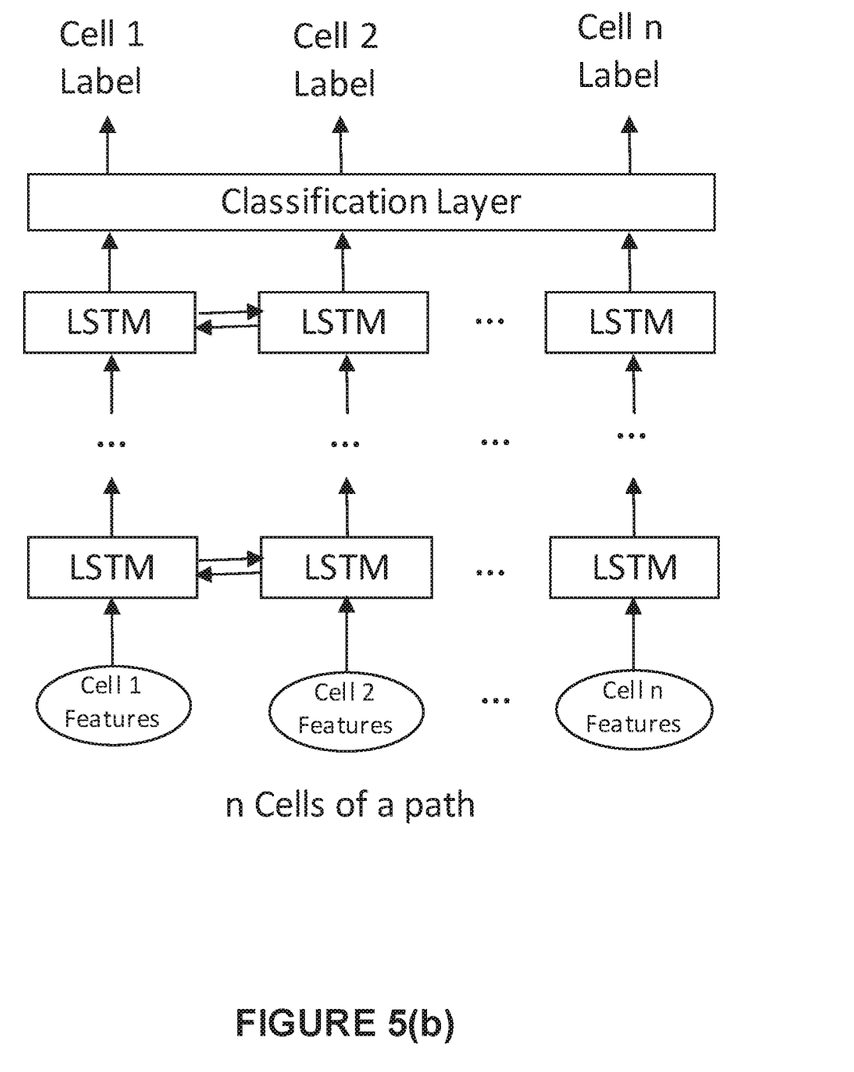
FIG. 5(b) illustrates an example of the learning network used in the method according to an embodiment of present disclosure.

FIG. 5(b) illustrates an example of the learning network used in the method according to an embodiment of present disclosure. As shown in FIG. 5(b), there are n cells on a path and thus a sequence of cell-wise features, including cell 1 features, cell 2 features, ..., cell n features, may be fed into a sequence-to-sequence neural network. In some embodiments, the sequence-to-sequence neural network may include at least one of a sequential neural network (such as the sequential (multilayer) long short-term memory (LSTM) neural network in FIG. 5(b)) and a tree-structure neural network (such as a tree-structure bidirectional LSTN neural network in FIG. 5(e)). Then, the sequence-to-sequence neural network may determine a sequence of cell labels, i.e., cell 1 label, cell 2 label, ..., cell n label, by means of a classification layer, e.g., fully connected layers.

Figure 5C:
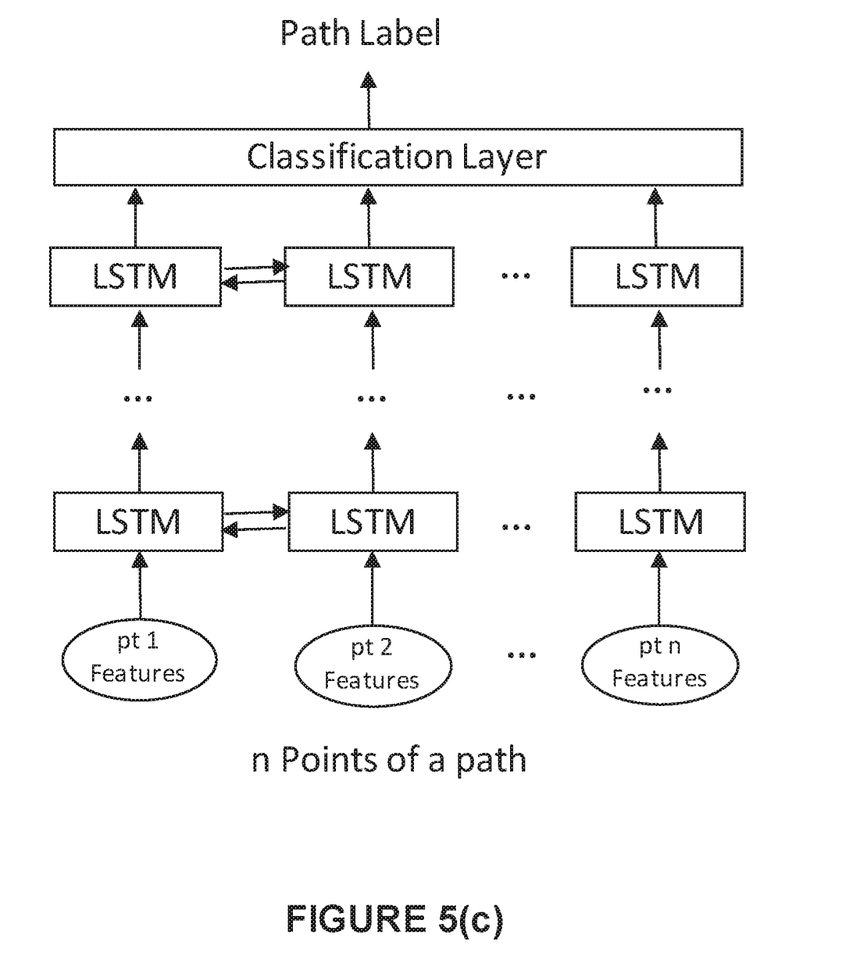
FIG. 5(c) illustrates an example of the learning network used in the method according to an embodiment of present disclosure.

FIG. 5(c) illustrates an example of the learning network used in the method according to an embodiment of present disclosure. As shown in FIG. 5(c), there are n points on a path and thus a sequence of point-wise features, including pt 1 features, pt 2 features, ..., pt n features, may be fed into a neural network having fully connected layers as the classification layer, so as to generate a path label. In some embodiments, the neural network may be a sequential (multilayer) LSTM neural network. As shown in FIG. 5(b) and FIG. 5(c), the sequence-to-sequence neural network is illustrated as a sequential multilayer LSTM neural network, with unidirectional information transmission between adjacent layers but bidirectional information transmission between adjacent nodes on the same layer. But the sequence-to-sequence neural network is not limited to this example, it may adopt other frameworks.

Figure 5D:
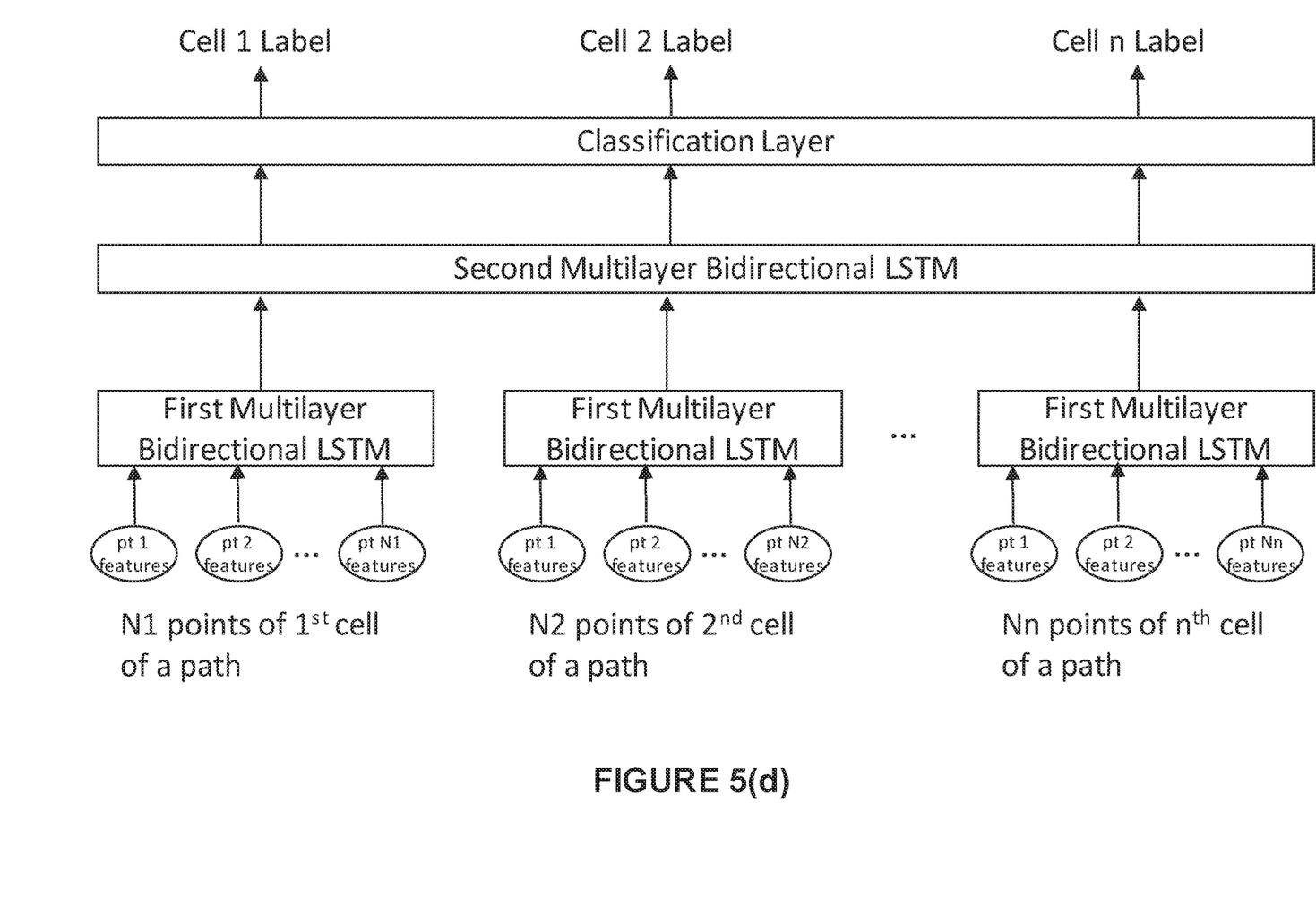
FIG. 5(d) illustrates an example of the learning network used in the method according to an embodiment of present disclosure.

FIG. 5(d) illustrates an example of the learning network used in the method according to an embodiment of present disclosure. The learning network as shown in FIG. 5(d) differs from that shown in FIG. 5(c) in that it learns the relationships between the point-wise features of a sequence of points on a sequence of n cells on a path and the sequence of the cell labels of the n cells level by level. Particularly, at the bottom layer, for the $i^{th}$ (i=1, 2, ..., n) cell of a sequence of n cells on the path, Ni points thereon are sampled and the point-wise features of the Ni points may be fed into the corresponding first multilayer bidirectional LSTM neural network to generate the corresponding cell-wise feature. For example, there may be N3 sampling points on the $3^{rd}$ cell, and pt 1 features, pt 2 features, ..., pt N3 features, may be extracted and fed into the first multilayer bidirectional LSTM neural network for the $3^{rd}$ cell, so as to generate the cell-wise feature(s) of the $3^{rd}$ cell. Then, the cell-wise features of the n cells may be fed as a sequence into a second multilayer bidirectional LSTM neural network, so as to generate a sequence of cell labels for the n cells by means of the classification layer. By means of the first multilayer bidirectional LSTM neural network, the learning network firstly considers and learns the mutual influences among the points in the corresponding cell; and by means of the second multilayer bidirectional LSTM neural network, the learning network considers and learns the mutual influences among the cells in the path. The learning network adopts a hierarchical framework of sequence-to-sequence mapping, which complies with the function mechanism of the physiological tree structure, and may generate the anatomical labels more accurately.

Figure 5E:
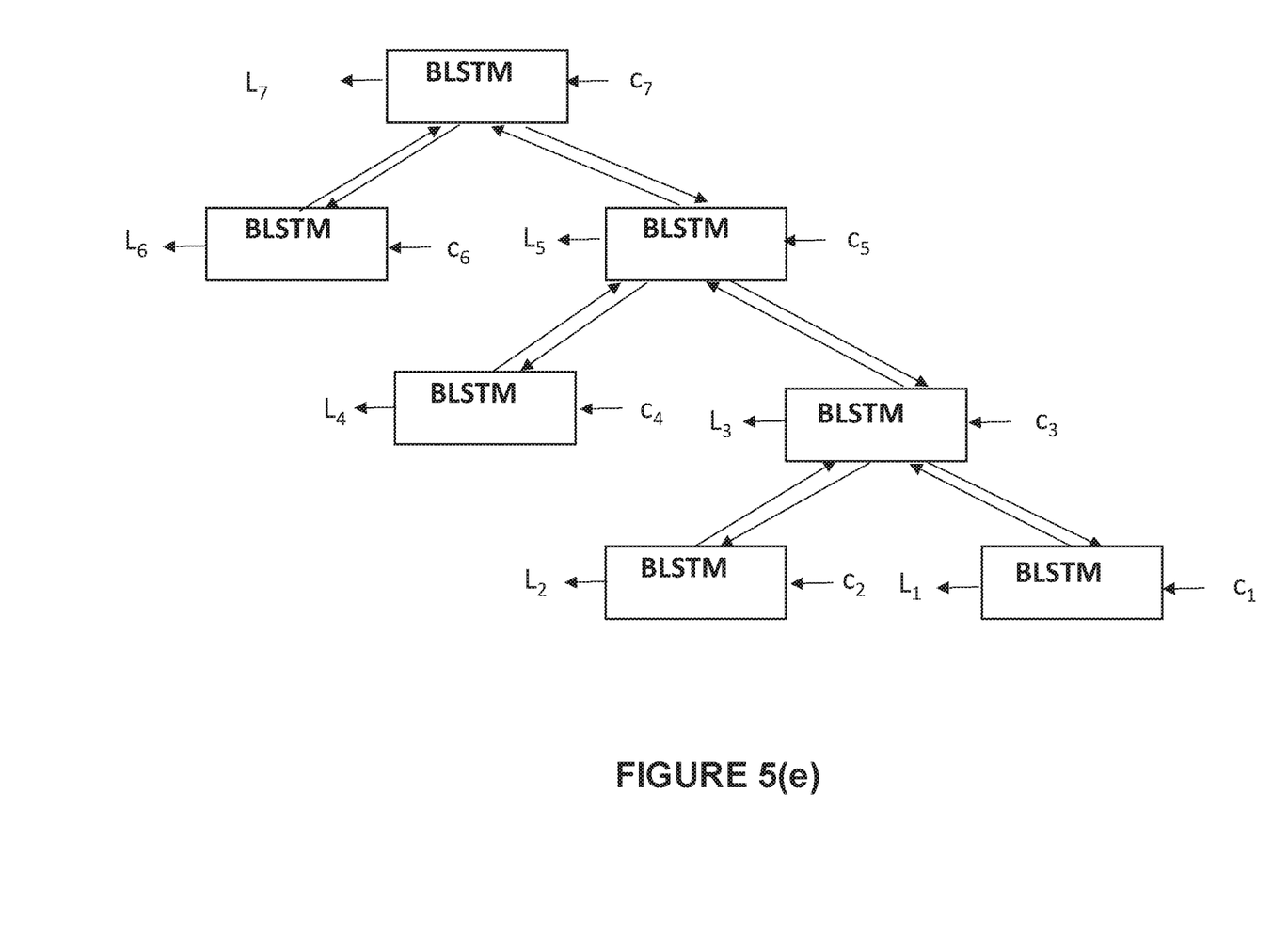
FIG. 5(e) illustrates an example of the learning network used in the method according to an embodiment of present disclosure.

FIG. 5(e) illustrates an example of the learning network used in the method according to an embodiment of present disclosure. As shown in FIG. 5(e), the learning network adopts a tree structure comprised of 7 nodes, with each node configured as a bidirectional LSTM neural network (BLSTM). The cell-wise features $c_1 \sim c_7$ may be fed into the nodes of the tree structure of BLSTMs one to one, and the tree structure of BLSTMs may generate the corresponding cell-wise labels $L_1 \sim L_7$.

Figure 6:
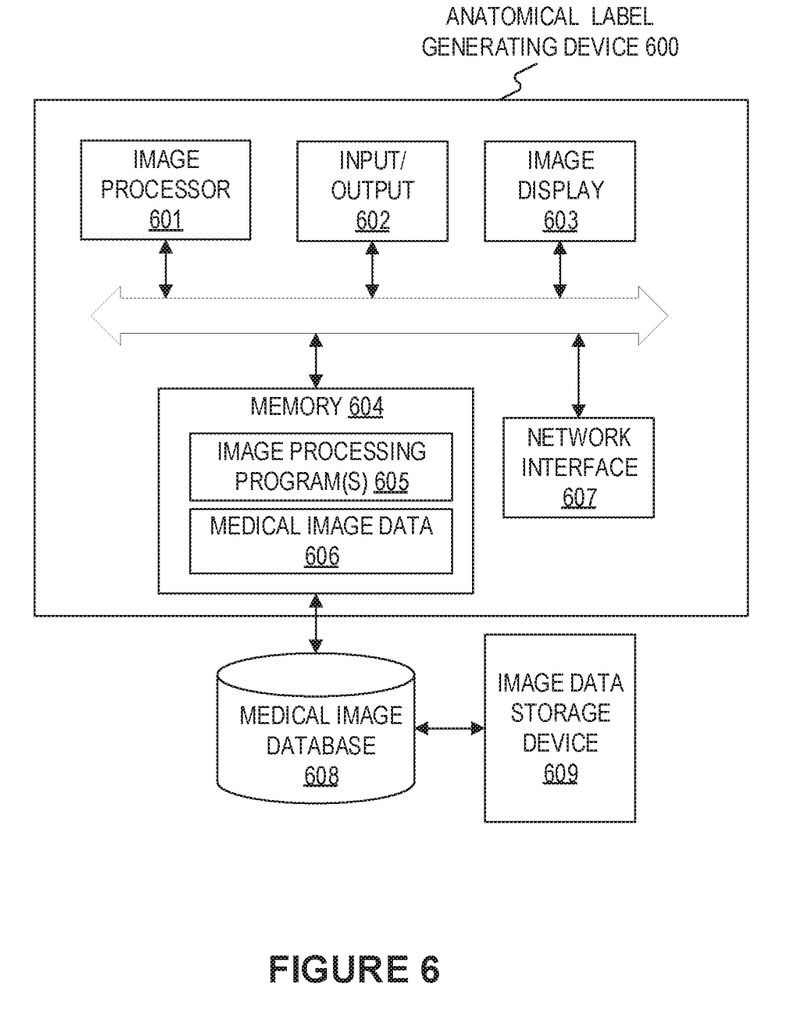
FIG. 6 depicts a block diagram illustrating an exemplary anatomical label generating device, according to an embodiment of present disclosure.

FIG. 6 illustrates a block diagram of an exemplary anatomical label generating device 600 according to an embodiment of present disclosure. The anatomical label generating device 600 may include a network interface 607, by means of which the anatomical label generating device 600 may be connected to the network (not shown), such as but not limited to the local area network in the hospital or the Internet. The network can connect the anatomical label generating device 600 with external devices such as an image acquisition device (not shown), medical image database 608, and an image data storage device 609. An image acquisition device may use any type of imaging modalities, such as but not limited to CT, digital subtraction angiography (DSA), MRI, functional MRI, dynamic contrast enhanced-MRI, diffusion MRI, spiral CT, cone beam computed tomography (CBCT), positron emission tomography (PET), single-photon emission computed tomography (SPECT), X-ray, optical tomography, fluorescence imaging, ultrasound imaging, radiotherapy portal imaging.

In some embodiments, the anatomical label generating device 600 may be a dedicated intelligent device or a general-purpose intelligent device. For example, the device 600 may be a computer customized for image data acquisition and image data processing tasks, or a server placed in the cloud. For example, the device 600 may be integrated into the image acquisition device. Optionally, the image processing program(s) 605 in the device 600 may executed by a 3D reconstruction unit for reconstructing the 3D model of the vessel based on the vessel image data acquired by the image acquisition device.

The anatomical label generating device 600 may include an image processor 601 and a memory 604, and may additionally include at least one of an input/output 602 and an image display 603.

The image processor 601 may be a processing device that includes one or more general processing devices, such as a microprocessor, a central processing unit (CPU), a graphics processing unit (GPU), and the like. More specifically, the image processor 601 may be a complex instruction set computing (CISC) microprocessor, a reduced instruction set computing (RISC) microprocessor, a very long instruction word (VLIW) microprocessor, a processor running other instruction sets, or a processor that runs a combination of instruction sets. The image processor 601 may also be one or more dedicated processing devices such as application specific integrated circuits (ASICs), field programmable gate arrays (FPGAs), digital signal processors (DSPs), system-on-chip (SoCs), and the like. As would be appreciated by those skilled in the art, in some embodiments, the image processor 601 may be a special-purpose processor, rather than a general-purpose processor. The image processor 601 may include one or more known processing devices, such as a microprocessor from the Pentium™ Core™ Xeon™, or Itanium® family manufactured by Intel™, the Turion™, Athlon™ Sempron™, Opteron™, FX™, Phenom™ family manufactured by AMD™, or any of various processors manufactured by Sun Microsystems. The image processor 601 may also include graphical processing units such as a GPU from the GeForce®, Quadro®, Tesla® family manufactured by Nvidia™, GMA, Iris™ family manufactured by Intel™, or the Radeon™ family manufactured by AMD™. The image processor 601 may also include accelerated processing units such as the Desktop A-4 (6, 6) Series manufactured by AMD™, the Xeon Phi™ family manufactured by Intel™. The disclosed embodiments are not limited to any type of processor(s) or processor circuits otherwise configured to meet the computing demands of identifying, analyzing, maintaining, generating, and/or providing large amounts of imaging data or manipulating such imaging data to acquire (receive directly or reconstruct) a 3D model and a 3D skeleton line of a physiological tree structure, extract a selectable level of geometrical features from the 3D model along the 3D skeleton line, and/or generate the anatomical labels, or to manipulate any other type of data consistent with the disclosed embodiments. In addition, the term "processor" or "image processor" may include more than one processor, for example, a multi-core design or a plurality of processors each having a multi-core design. The image processor 601 can execute sequences of computer program instructions, stored in memory 604, to perform various operations, processes, methods disclosed herein.

The image processor 601 may be communicatively coupled to the memory 604 and configured to execute computer-executable instructions stored therein. The memory 604 may include a read only memory (ROM), a flash memory, random access memory (RAM), a dynamic random-access memory (DRAM) such as synchronous DRAM (SDRAM) or Rambus DRAM, a static memory (e.g., flash memory, static random access memory), etc., on which computer executable instructions are stored in any format. In some embodiments, the memory 604 may store computer-executable instructions of one or more image processing program(s) 605. The computer program instructions can be accessed by the image processor 601, read from the ROM, or any other suitable memory location, and loaded in the RAM for execution by the image processor 601. For example, memory 604 may store one or more software applications. Software applications stored in the memory 604 may include, for example, an operating system (not shown) for common computer systems as well as for soft-controlled devices.

Further, memory 604 may store an entire software application or only a part of a software application (e.g. the image processing program (s) 605) to be executable by the image processor 601. In addition, the memory 604 may store a plurality of software modules, for implementing the respective steps of the method for generating anatomical labels for the physiological tree structure based on images of the physiological tree structure or the process for training the label generation model consistent with the present disclosure. For example, the generation model training unit 201, the generation unit 202, the feature extracting unit 204, and the 3D reconstruction unit 205 (as shown in FIG. 2), may be implemented as soft modules stored on the memory 604. For another example, at least the generation unit 202 and the feature extracting unit 204 are implemented as soft modules stored on the memory 604, the generation model training unit 201 may be located remote from the anatomical label generating device 600 and communicate with the generation unit 202 to enable it receive the updated generation model, which is already trained by the generation model training unit 201 with the training data from the training data database 203 (in an off-line training process) and/or from the generation unit 202 (i.e., the anatomical labels automatically generated therefrom (with or without manual correction by the user) together with the corresponding extracted geometrical features) (in an on-line training process), for generating the anatomical labels along the 3D centerline of the tree structures.

Besides, the memory 604 may store data generated/buffered when a computer program is executed, for example, medical image data 606, including the medical images transmitted from image acquisition device(s), medical image database 608, image data storage device 609, etc. In some embodiments, medical image data 606 may include the received image(s) of the physiological tree structure, for which 3D model reconstruction, 3D skeleton line extraction, the automatic geometrical feature extraction and further anatomical label generation are to be implemented by the image processing program(s) 605.

Besides, the image processor 601 may execute the image processing program(s) 605 to implement a method for generating anatomical labels for a physiological tree structure, then associate the corresponding extracted geometrical features with the anatomical labeling results, and transmit the same into the memory 604, especially as the medical image data 606 therein. In this manner, each on-line label generating process generates a piece of fresh training data to update the medical image data 606. By means of executing the generating model training unit 201 as shown in FIG. 2, the image processor 601 may train the label generation model in an on-line manner to update the existing parameters (such as the weights) in the trained label generation model. In some embodiments, the updated parameters of the trained label generation model may be stored in the medical image data 606, which may then be used in the next anatomical label generation for the same patient. Therefore, if the image processor 601 determines that the anatomical label generating device 600 has performed a label generation for the present patient, then the latest updated label generation model may be recalled and used directly.

In some embodiments, the image processor 601, upon performing an on-line label generating process, may associate the 3D model (the 3D model reconstructed based on the 2D images, or a 3D volumetric image) of the physiological tree structure together with the automatically (or semi-automatically) generated anatomical labels as medical image data 606 for presenting and/or transmitting. In some embodiments, the 3D model together with the generated anatomical labels may be displayed on the image display 603 for the user's review. In some embodiments, the medical image data by associating the 3D model with the generated anatomical labels may be transmitted to the medical image database 608, so as to be accessed, obtained, and utilized by other medical devices, if needed.

In some embodiments, the image data storage device 609 may be provided to exchange image data with the medical image database 608, and the memory 604 may communicate with the medical image database 608 to obtain the images and/or 3D models and/or skeleton lines of the physiological tree structure of the current patient. For example, the image data storage device 609 may reside in other medical image acquisition devices, e.g., a CT which performs scan on the patients. The slices of the patients may be transmitted and saved into the medical image database 608, and the anatomical label generating device 600 may retrieve slices of a specific patient from the medical image database 608 and generate anatomical labels for the specific patient.

In some embodiments, the memory 604 may communicate with the medical image database 608 to transmit and save the extracted geometrical features associated with the generated anatomical labels into the medical image database 608 as a piece of training data, which may be used for off-line training of the reference label generation model and/or the specific label generation model (specific for a patient) as described above.

Besides, the parameters of the trained reference label generation model and/or the specific label generation model may be stored on the medical image database 608, to be accessed, obtained, and utilized by other anatomical label generating devices, if needed. In this manner, confronting a patient, the image processor 601 may retrieve a trained reference label generation model of the corresponding population and/or the specific label generation model for the patient, so as to generate the anatomical labels based on the retrieved trained model.

In some embodiments, the anatomical label generation model (especially the learning network) may be stored in the memory 604. Optionally, the learning network may be stored in a remote device, a separate database, such as the medical image database 608, distributed devices, and may be used by the image processing program(s) 605.

Besides displaying the medical images, the image display 603 may also display other information, such as the generated anatomical labels adjacent to the corresponding part of the physiological tree structure by mapping the generated anatomical labels to the corresponding part. For example, the image display 603 may be an LCD, a CRT, or an LED display.

The input/output 602 may be configured to allow the anatomical label generating device 600 to receive and/or send data. The input/output 602 may include one or more digital and/or analog communication devices that allow the device 600 to communicate with a user or other machine and device. For example, the input/output 602 may include a keyboard and a mouse that allow the user to provide an input.

In some embodiments, the image display 603 may present a user interface, so that the user, by means of the input/output 602 together with the user interface, may conveniently and intuitively correct (such as edit, move, modify, etc.) the generated anatomical labels.

The network interface 607 may include a network adapter, a cable connector, a serial connector, a USB connector, a parallel connector, a high-speed data transmission adapter such as optical fiber, USB 6.0, lightning, a wireless network adapter such as a Wi-Fi adapter, a telecommunication (6G, 4G/LTE, etc.) adapters. The device 600 may be connected to the network through the network interface 607. The network may provide the functionality of local area network (LAN), a wireless network, a cloud computing environment (e.g., software as a service, platform as a service, infrastructure as a service, etc.), a client-server, a wide area network (WAN), and the like.

Various operations or functions are described herein, which may be implemented as software code or instructions or defined as software code or instructions. Such content may be source code or differential code ("delta" or "patch" code) that can be executed directly ("object" or "executable" form). The software code or instructions may be stored in computer readable storage medium, and when executed, may cause a machine to perform the described functions or operations and include any mechanism for storing information in the form accessible by a machine (e.g., computing device, electronic system, etc.), such as recordable or nonrecordable media (e.g., read-only memory (ROM), random access memory (RAM), disk storage media, optical storage media, flash memory devices, etc.).

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments.

Exemplary methods described herein can be machine or computer-implemented at least in part. Some examples can include a non-transitory computer-readable medium or machine-readable medium encoded with instructions operable to configure an electronic device to perform methods as described in the above examples. An implementation of such methods can include software code, such as microcode, assembly language code, a higher-level language code, or the like. The various programs or program modules can be created using a variety of software programming techniques. For example, program sections or program modules can be designed in or by means of Java, Python, C, C++, assembly language, or any known programming languages. One or more of such software sections or modules can be integrated into a computer system and/or computer-readable media. Such software code can include computer readable instructions for performing various methods. The software code may form portions of computer program products or computer program modules. Further, in an example, the software code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including by reordering steps or inserting or deleting steps. It is intended, therefore, that the descriptions be considered as examples only, with a true scope being indicated by the following claims and their full scope of equivalents.

The above description is intended to be illustrative, and not restrictive. For example, the above-described examples (or one or more aspects thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A computer-implemented method for generating anatomical labels for a physiological tree structure, comprising the following steps:
   receiving a 3D model and a 3D skeleton line of the physiological tree structure, wherein the 3D model is reconstructed based on medical image data of the physiological tree structure acquired by an imaging device;
   selecting at least one level for extracting geometrical features from a pool of selectable levels including a higher level and a lower level, geometrical features in the higher level having a lower granular accuracy than geometrical features in the lower level;
   extracting, by a processor, geometrical features from the 3D model of the physiological tree structure along the 3D skeleton line at the selected at least one level; and
   generating, by the processor, anatomical labels for the physiological tree structure at a level equal to or higher than the selected level of extracted geometrical features, wherein the anatomical labels are generated using a trained sequence-to-sequence network based on a sequence of the extracted geometrical features.

2. The computer-implemented method of claim 1, wherein the geometrical features include multiple types of geometrical features at each selected level.

3. The computer-implemented method of claim 1, wherein the selected at least one level includes a plurality of levels, and wherein extracting geometrical features includes extracting geometrical features at each of the plurality of levels.

4. The computer-implemented method of claim 1, wherein the selectable levels include levels corresponding to point-wise geometrical features, cell-wise geometrical features, and path-wise geometrical features.

5. The computer-implemented method of claim 1, wherein the physiological tree structure is a tree structure of any one of blood vessels, tracheal pathway, lymphatic vessels, and nervous tissue.

6. The computer-implemented method of claim 1, wherein the physiological tree structure is a tree structure of blood vessel, the 3D skeleton line is a centerline.

7. The computer-implemented method of claim 1, wherein the level for extracting geometrical features is selected based on at least one of the calculating speed, computing resource, and granular accuracy.

8. The computer-implemented method of claim 1, wherein the trained sequence-to-sequence network is a neural network including a classification layer.

9. The computer-implemented method of claim 8, wherein the neural network includes at least one of a sequential multi-layer neural network and a tree-structure neural network.

10. The computer-implemented method of claim 9, wherein generating anatomical labels further includes:
    generating a sequence of anatomical labels for the physiological tree structure using a trained sequential LSTM multi-layer neural network or a trained tree-structure LSTM neural network based on the extracted geometrical features.

11. The computer-implemented method of claim 1, wherein the trained sequence-to-sequence network is trained in an online process or an offline process.

12. The computer-implemented method of claim 1, further comprising:
mapping the generated anatomical labels to corresponding parts of the physiological tree structure.

13. The computer-implemented method of claim 12, further comprising:
presenting the generated anatomical labels adjacent to the corresponding parts of the physiological tree structure on a user interface for a user to modify the generated anatomical labels.

14. The computer-implemented method of claim 12, further comprising:
receiving modified anatomical labels from the user; and
updating the trained sequence-to-sequence network using the extracted geometrical features and the modified anatomical labels as a training dataset.

15. A device for generating anatomical labels for a physiological tree structure, comprising:
an interface configured to receive medical image data of the physiological tree structure acquired by an imaging device; and
a processor configured to:
reconstruct a 3D model and extract a 3D skeleton line of the physiological tree structure based on the received medical image data;
select at least one level for extracting geometrical features from a pool of selectable levels including a higher level and a lower level, geometrical features in the higher level having a lower granular accuracy than geometrical features in the lower level;
extract geometrical features from the 3D model of the physiological tree structure along the 3D skeleton line at the selected at least one level; and
generate anatomical labels for the physiological tree structure at a level equal to or higher than the selected level of the extracted geometrical features, wherein the anatomical labels are generated using a trained sequence-to-sequence network based on a sequence of the extracted geometrical features.

16. The device of claim 15, wherein the imaging device uses an imaging modality selected from a group of CT, digital subtraction angiography (DSA), MRI, functional MRI, dynamic contrast enhanced MRI, diffusion MRI, spiral CT, cone beam computed tomography (CBCT), positron emission tomography (PET), single-photon emission computed tomography (SPECT), X-ray imaging, optical tomography, fluorescence imaging, ultrasound imaging, radiotherapy portal imaging.

17. A non-transitory computer readable medium having instructions stored thereon, the instructions, when executed by a processor, cause the processor to perform a method for generating anatomical labels for a physiological tree structure, the method comprising:
receiving a 3D model and a 3D skeleton line of the physiological tree structure, wherein the 3D model is restructured based on medical image data of the physiological tree structure acquired by an imaging device;
selecting at least one level for extracting geometrical features from a pool of selectable levels including a higher level and a lower level, geometrical features in the higher level having a lower granular accuracy than geometrical features in the lower level;
extracting geometrical features from the 3D model of the physiological tree structure along the 3D skeleton line at the selected at least one level; and
generating anatomical labels for the physiological tree structure at a level equal to or higher than the selected level of the extracted geometrical features, wherein the anatomical labels are generated using a trained sequence-to-sequence network based on a sequence of the extracted geometrical features.

18. The non-transitory computer readable medium of claim 17, wherein the selectable levels include levels corresponding to point-wise geometrical features, cell-wise geometrical features, and path-wise geometrical features.

19. The non-transitory computer readable medium of claim 17, wherein the physiological tree structure is a tree structure of blood vessel, the 3D skeleton line is a centerline.

* * * * *